(12) United States Patent
Li et al.

(10) Patent No.: US 9,718,836 B2
(45) Date of Patent: Aug. 1, 2017

(54) ARTIFICIAL ANTIGEN OF AFLATOXIN BIOSYNTHETIC PRECURSOR STERIGMATOCYSTIN AND METHOD FOR PREPARING SAME

(71) Applicant: OILCROPS RESEARCH INSTITUTE OF CHINESE ACADEMY OF AGRICULTURE SCIENCES, Wuhan, Hubei (CN)

(72) Inventors: Peiwu Li, Hubei (CN); Qi Zhang, Hubei (CN); Min Li, Hubei (CN); Fei Ma, Hubei (CN); Xiaoxia Ding, Hubei (CN)

(73) Assignee: OILCROPS RESEARCH INSTITUTE OF CHINESE ACADEMY OF AGRICULTURE SCIENCES, Wuhan, Hubei (CN)

( * ) Notice: Subject to any disclaimer, the term of this patent is extended or adjusted under 35 U.S.C. 154(b) by 49 days.

(21) Appl. No.: 14/667,341

(22) Filed: Mar. 24, 2015

(65) Prior Publication Data

US 2015/0274846 A1    Oct. 1, 2015

(30) Foreign Application Priority Data

Mar. 26, 2014 (CN) .......................... 2014 1 0115645

(51) Int. Cl.
| | | |
|---|---|---|
| *A61K 39/02* | (2006.01) | |
| *A61K 39/00* | (2006.01) | |
| *A61K 39/385* | (2006.01) | |
| *C07D 493/14* | (2006.01) | |
| *A61K 31/335* | (2006.01) | |

(52) U.S. Cl.
CPC .......... *C07D 493/14* (2013.01); *A61K 31/335* (2013.01)

(58) Field of Classification Search
CPC ................................ A61K 39/00; A61K 39/02
USPC ................................ 424/184.1, 193.1, 234.1
See application file for complete search history.

*Primary Examiner* — Rodney P Swartz
(74) *Attorney, Agent, or Firm* — Tim Tingkang Xia, Esq.; Locke Lord LLP

(57) ABSTRACT

An artificial antigen of aflatoxin biosynthetic precursor Sterigmatocystin (ST) and a method for preparing same. Firstly, hydroxyacetic acid is reacted with the double bound of the difuran ring in the aflatoxin biosynthetic precursor ST, yielding an aflatoxin biosynthetic precursor ST hapten with an active carboxymethoxy group. Secondly, a carboxyl group on the ST hapten is attached to an amino group on a carrier protein. At last, the artificial antigen of aflatoxin biosynthetic precursor ST is obtained by dialysis and lyophilize.

3 Claims, 1 Drawing Sheet

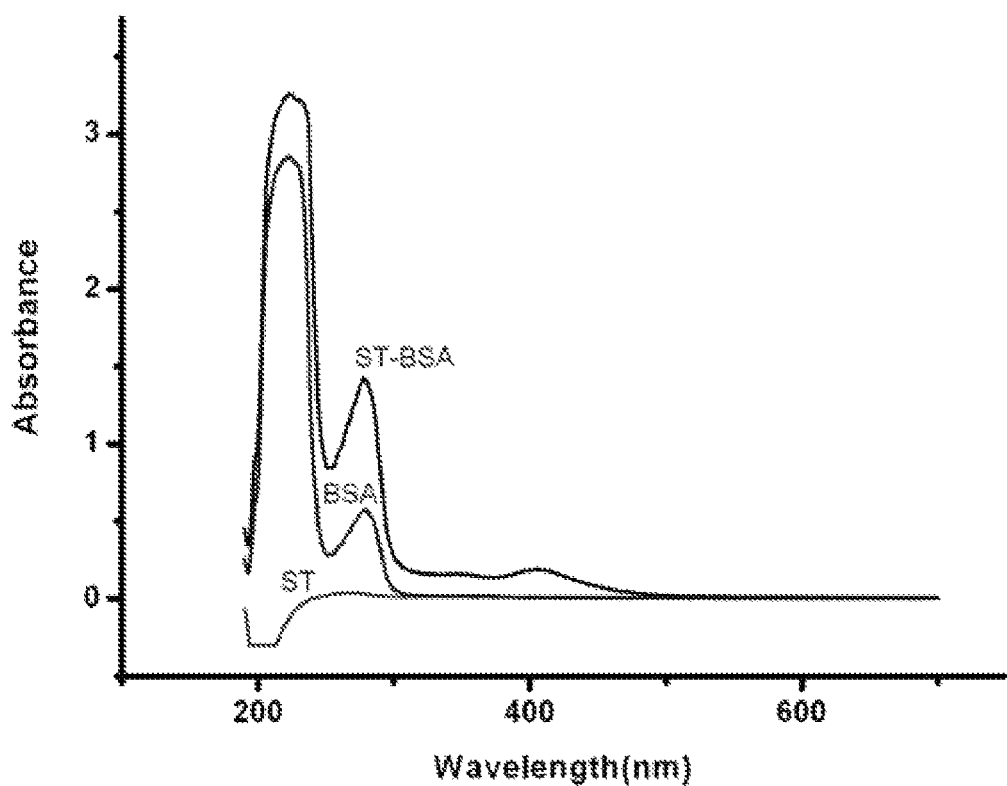

ARTIFICIAL ANTIGEN OF AFLATOXIN BIOSYNTHETIC PRECURSOR STERIGMATOCYSTIN AND METHOD FOR PREPARING SAME

CROSS-REFERENCE TO RELATED APPLICATION

This non-provisional application claims priority under 35 U.S.C. §119(a) on Patent Application No. 201410115645.X filed in P.R. China on Mar. 26, 2014, the entire contents of which are hereby incorporated by reference.

Some references, if any, which may include patents, patent applications and various publications, may be cited and discussed in the description of this invention. The citation and/or discussion of such references, if any, is provided merely to clarify the description of the present invention and is not an admission that any such reference is "prior art" to the invention described herein. All references listed, cited and/or discussed in this specification are incorporated herein by reference in their entireties and to the same extent as if each reference was individually incorporated by reference.

FIELD OF THE INVENTION

The present invention relates to an artificial antigen of aflatoxin biosynthetic precursor ST and a method for preparing same.

BACKGROUND OF THE INVENTION

A fungal toxin is a secondary metabolite secreted by a toxin-producing fungus and a natural toxic compound capable of causing various injuries on the human being and the livestock. Among fungal toxins ever found, aflatoxin (hereinafter referred to as "AFT") is the most toxic fungal toxin, and its toxicity, carcinogenicity and contamination frequency all rank the first among biological toxins. Sterigmatocystin, i.e., ST, is a precursor for aflatoxin synthesis and produced mainly by the fungi such as *Aspergillus versicolor*, *Aspergillus flavus*, *Aspergillus nidulans*, and *Aspergillus rugulosus*, etc. ST may contaminate most of grains and forage grasses, and in particular severely contaminate wheat, maize, peanut, forage grasses. The basic structure of aflatoxin biosynthetic precursor ST consists of a difuran ring in connection with xanthone. The precursor has a structure similar to that of aflatoxin, and has toxicity that is second only to that of aflatoxin. Toxicity of ST includes hepatotoxicity, nephrotoxicity, cytogenetic toxicity and potent carcinogenicity. It enters into the human food chain after contaminating foods and feeds, and poses a threat to the health and safety of human. The hazard degree has a positive correlation with the intake of aflatoxin biosynthetic precursor ST. Since China is an area where there is more severe contamination with aflatoxin biosynthetic precursor ST, one of the key points to fortify the food safety is to improve detection of aflatoxin biosynthetic precursor ST in food products and feeds. Accordingly, it is necessary to determine the content of ST in cereals and finished products thereof suspected to be contaminated with the aflatoxin biosynthetic precursor ST.

Currently, methods for detecting aflatoxin biosynthetic precursor ST mainly include thin-layer chromatography (TLC) and liquid chromatography. TLC is easy to operate, and does not require complex and precise instrumentation, but has low sensitivity and low accuracy. Using TLC, a lower limit of detection of aflatoxin biosynthetic precursor ST in rice, maize, and wheat samples is 25 μg/kg and that in soybean and peanut samples is 50 μg/kg. In the recent years, high-performance liquid chromatography (HPLC) has been used widely in the detection of fungal toxins and has also been reported for detecting the aflatoxin biosynthetic precursor ST. However, the application of the HPLC in detection at the basic level has been limited by tedious pre-processing, expensive instrumentation, requirements for stringent operation environment, and professional operators, etc. Therefore, there is a pressing need in the detection field in China to study and develop novel techniques for rapid detection of aflatoxin biosynthetic precursor ST, which is of importance on guaranteeing the safety in food consumption in China.

Immunological analysis techniques have been increasingly the focus of rapid detection techniques for pollutants such as aflatoxin, due to advantages such as high sensitivity, short detection time, and easy to operate, etc. However, there are few reports on rapid detection techniques for aflatoxin biosynthetic precursor ST. Antigens and antibodies are the core reagents and the technological sources in immunological analysis techniques. The aflatoxin biosynthetic precursor ST has a molecular weight of 324, belongs to small molecule compounds (≤1000) and is incapable of directly stimulating an animal to produce antibodies. Only after covalently coupled to a carrier protein such as bovine serum protein (BSA), egg white albumin (OVA), and polylysine, etc., would aflatoxin be converted into a complete antigen with both reactogenicity and immunogenicity which can stimulate an animal to produce antibodies. Currently, antibodies obtained by immunization with an artificial antigen of aflatoxin biosynthetic precursor ST (the synthesis method is mainly sodium borohydride reduction) have been reported to be low in sensitivity and poor in specificity.

SUMMARY OF THE INVENTION

In one aspect, the present invention relates to an artificial antigen of aflatoxin biosynthetic precursor ST and a method for preparing the artificial antigen. Antibodies with high sensitivity and strong specificity can be produced against aflatoxin biosynthetic precursor ST. The preparation process of the artificial antigen is simple and practicable, is easy in scale up production, and can be used in different applications.

In one embodiment, an artificial antigen of aflatoxin biosynthetic precursor ST is obtained by coupling the aflatoxin biosynthetic precursor ST to a carrier protein. The coupling process includes: opening a double bound of the difuran ring of the aflatoxin biosynthetic precursor ST, and connecting an active carboxymethoxy group, then connecting the carboxyl on the active carboxymethoxy group to the amino group on the carrier protein.

In one embodiment, a method for preparing the artificial antigen of aflatoxin biosynthetic precursor ST includes: firstly, reacting hydroxyacetic acid with the double bound of the difuran ring in the aflatoxin biosynthetic precursor ST, to obtain an aflatoxin biosynthetic precursor ST hapten with an active carboxymethoxy group; then via an active ester procedure, attaching the carboxyl group on the aflatoxin biosynthetic precursor ST hapten to an amino group on the carrier protein at room temperature; and at last, dialyzing and lyophilizing to obtain the artificial antigen of aflatoxin biosynthetic precursor ST.

In one embodiment, the reaction process of the hydroxyacetic acid with the double bound of the difuran ring of the aflatoxin biosynthetic precursor ST is as follows: firstly, weighting 0.1-1 g of hydroxyacetic acid and dissolving it in 0.4-4 mL of trifluoroacetic acid; secondly, weighing 1-10 mg of the aflatoxin biosynthetic precursor ST and dissolving it in 0.4-4 mL of acetonitrile, to obtain a solution of aflatoxin biosynthetic precursor ST in acetonitrile; then, drawing the solution of aflatoxin biosynthetic precursor ST in acetonitrile with a syringe and pipetting the drawn solution gently into the mixture of hydroxyacetic acid/trifluoroacetic acid, where the reaction is run at room temperature for 4-6 h with stirring; after completion of the reaction, evaporating rotationally the solvent to yield a light yellowish green oily substance, which is the aflatoxin biosynthetic precursor ST hapten.

In one embodiment, the carboxyl group on the aflatoxin biosynthetic precursor ST hapten is attached to the amino group of the carrier protein as follows: weighting 1-10 mg of aflatoxin biosynthetic precursor ST hapten and 4-30 mg of N-hydroxylsuccinimide and placing them into a reaction flask and reacting for 1-2 h; weighing 7-45 mg of carbodiimide and dissolving it in 0.2-1.2 mL of 1,4-dioxohextane, to obtain a solution of carbodiimide in 1,4-dioxohextane, then adding the solution dropwise into the reaction flask and reacting at room temperature for 4-5 h until a white precipitate is generated in the reaction flask, after completion of the reaction, allowing the reaction mixture to stand at room temperature overnight, and on the next day, centrifuging to obtain the supernatant; adding the obtained supernatant dropwise into a phosphate buffered saline (PBS) solution having 4-30 mg of the carrier protein dissolved therein, after adding the supernatant, running the reaction for 4-5 h, to obtain an complete antigen of aflatoxin biosynthetic precursor ST in aqueous phase.

In one embodiment, the PBS solution is a 0.2 mol/L, pH8.0 phosphate buffer with a volume of 5-8 mL.

In one embodiment, the dialyzing and lyophilzing process is as follows: filling and sealing the complete antigen of aflatoxin biosynthetic precursor ST in aqueous phase into a dialysis bag, and dialyzing against 0.01-0.02 mol/L, pH8.0 phosphate buffer for a total of 3 days, where the dialysis solution is replaced once every 4-12 h; after completion of the last dialysis, separating the solution in the dialysis bag into fractions, and lyophilizing the fractions, to obtain the artificial antigen of aflatoxin biosynthetic precursor ST.

In one embodiment, the carrier protein may be selected from biological proteins or synthetic polypeptides, such as bovine serum albumin, egg white albumin, hemocyanin, and polylysine.

In one embodiment, a method for preparing the artificial antigen of aflatoxin biosynthetic precursor ST includes:

(1) weighing 0.1 g of commercially-available hydroxyacetic acid and dissolving it in 0.4 mL of trifluoroacetic acid; weighing 1 mg of aflatoxin biosynthetic precursor ST and dissolving it in 0.4 mL of acetonitrile to obtain a solution of aflatoxin biosynthetic precursor ST in acetonitrile; drawing the solution of aflatoxin biosynthetic precursor ST in acetonitrile with a syringe, pipetting gently the solution into the mixture of hydroxyacetic acid/trifluoroacetic acid, reacting at room temperature for 4 h with stirring; evaporating the solvent rotationally, to obtain a light yellowish green oily substance which is the aflatoxin biosynthetic precursor ST hapten;

(2) weighing 1 mg of aflatoxin biosynthetic precursor ST hapten and 4 mg of N-hydroxylsuccinimide, placing them in a reaction flask and reacting for 1 h; weighing 7 mg of carbodiimide and dissolving it in 0.2 mL of 1,4-dioxohextane to obtain a solution of carbodiimide in 1,4-dioxohextane, then adding the solution dropwise into the reaction flask and reacting at room temperature for 4 h until a white precipitate is generated in the reaction flask; after completion of the reaction, allowing the reactants to stand at room temperature overnight, and in the next day, centrifuging at 8000 r/min for 5 min and taking the supernatant; weighing 4 mg of bovine serum albumin and dissolving it in 5 mL 0.2 mol/L, pH8.0 PBS buffer, adding the above-mentioned supernatant dropwise into the PBS solution containing bovine serum albumin, after the sample addition is completed, running the reaction for 4 h to obtain an complete antigen of aflatoxin biosynthetic precursor ST in aqueous phase; and (3) filling and enclosing the complete antigen of aflatoxin biosynthetic precursor ST in aqueous phase from the above-mentioned step (2) into a dialysis bag and dialyzing against 0.01 mol/L, pH8.0 PBS buffer for a total of 3 days, the dialyzing solution is replaced once every 12 h; after completion of the last dialysis, the solution in the dialysis bag is separated to fractions into centrifuge tubes, and lyophilizing the fractions to obtain the artificial antigen of aflatoxin biosynthetic precursor ST, i.e., aflatoxin biosynthetic precursor ST-bovine serum albumin.

In one embodiment, using BSA as the carrier protein, the synthesis route of coupling aflatoxin biosynthetic precursor ST and carrier protein to obtain the artificial antigen of aflatoxin biosynthetic precursor ST (aflatoxin biosynthetic precursor ST-BSA) is as follows:

Certain embodiments of the present invention, among other things, have the following beneficial advantages.

1. A double-carbon-atoms arm structure (i.e., carboxymethoxy) is connected to the ST molecule of the artificial antigen of aflatoxin biosynthetic precursor ST synthesized in the present invention. This facilitates sufficient exposure of the ST molecule on the carrier protein, reduces the effect of the coupled carrier protein on the immunogenicity of the artificial antigen, can have the mice immunized more efficiently to produce antibodies with high sensitivity and strong specificity against aflatoxin biosynthetic precursor ST, and is of important and practical significance in rapid detection of aflatoxin biosynthetic precursor ST with immunological analysis techniques. 2. The whole preparation process in the present invention is simple and practicable, does not need special instrumentation, has low cost, and thus is easy for scale up production and easy in widen applications. 3. The artificial antigen of aflatoxin biosynthetic precursor ST synthesized according to certain embodiments of the present invention is more stable.

These and other aspects of the present invention will become apparent from the following description of the preferred embodiment taken in conjunction with the following drawings, although variations and modifications therein may be effected without departing from the spirit and scope of the novel concepts of the disclosure.

BRIEF DESCRIPTION OF THE DRAWINGS

The accompanying drawings illustrate one or more embodiments of the invention and together with the written description, serve to explain the principles of the invention. Wherever possible, the same reference numbers are used throughout the drawings to refer to the same or like elements of an embodiment, and wherein:

FIG. 1 is an ultraviolet-visible spectrum continuous scanning profile in one embodiment of the present invention, in which ST is the ultraviolet-visible spectrum continuous scanning profile of aflatoxin biosynthetic precursor ST; BSA is the ultraviolet-visible spectrum continuous scanning profile of bovine serum albumin; and ST-BSA is the ultraviolet-visible spectrum continuous scanning profile of the artificial antigen of aflatoxin biosynthetic precursor ST.

DETAINED DESCRIPTION OF THE INVENTION

The present invention is more particularly described in the following examples that are intended as illustrative only since numerous modifications and variations therein will be apparent to those skilled in the art. Various embodiments of the invention are now described in detail. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention.

Furthermore, relative terms, such as "lower" or "bottom" and "upper" or "top," may be used herein to describe one element's relationship to another element.

As used herein, "around", "about", "substantially" or "approximately" shall generally mean within 20 percent, preferably within 10 percent, and more preferably within 5 percent of a given value or range. Numerical quantities given herein are approximate, meaning that the term "around", "about", "substantially" or "approximately" can be inferred if not expressly stated.

As used herein, the terms "comprising", "including", "carrying", "having", "containing", "involving", and the like are to be understood to be open-ended, i.e., to mean including but not limited to.

EXAMPLE 1

An Artificial Antigen of Aflatoxin Biosynthetic Precursor ST was Obtained by the Following Steps (1) 0.1 g of commercially-available hydroxyacetic acid (with water content of approximately 1%) was weighed and dissolved in 0.4 mL of trifluoroacetic acid; 1 mg of aflatoxin biosynthetic precursor ST was weighed and dissolved in 0.4 mL of acetonitrile; the solution of aflatoxin biosynthetic precursor ST in acetonitrile was drawn with a syringe, and pipetted gently into the mixture of hydroxyacetic acid/trifluoroacetic acid and reacted at room temperature (20° C.-30° C.) for 4 h with magnetic stirring; the solvent was evaporated rotationally, yielding a light yellowish green oily substance which was the aflatoxin biosynthetic precursor ST hapten.

(2) 1 mg of aflatoxin biosynthetic precursor ST hapten and 4 mg of N-hydroxylsuccinimide were weighed and placed into a reaction flask, and reacted at room temperature for 1 h with magnetic stirring; 7 mg of carbodiimide was weighed and dissolved in 0.2 mL of 1,4-dioxohextane; the solution of carbodiimide in 1,4-dioxohextane was added slowly dropwise into the reaction flask and reacted at room temperature for 4 h with magnetic stirring until a white precipitate was generated in the reaction flask; after completion of the reaction, the reactants were kept at room temperature overnight, in the next day, the reactants were subjected to centrifugation at 8000 r/min for 5 min, and the supernatant was obtained; 4 mg of bovine serum albumin (BSA) was weighed and dissolved in 5 mL of PBS buffer (0.2 mol/L, pH8.0), the above obtained supernatant was added dropwise into the solution of BSA in PBS; after finishing addition of the supernatant, the reaction was run for 4 h, yielding an complete antigen of aflatoxin biosynthetic precursor ST in aqueous phase.

(3) The complete antigen of aflatoxin biosynthetic precursor ST in aqueous phase obtained from the above-mentioned step (2) was sealed into a dialysis bag and dialyzed for a total of 3 days against 0.01 mol/L, pH8.0 phosphate buffer, where the dialysis solution was replaced once every 12 h; after completion of the last dialysis, the solution in the dialysis bag was divided into fractions, placed in centrifuge tubes, and lyophilized to yield the artificial antigen of aflatoxin biosynthetic precursor ST. The ultraviolet-visible spectrum continuous scanning profile of the above artificial antigen can be seen in FIG. 1.

EXAMPLE 2

An Artificial Antigen of Aflatoxin Biosynthetic Precursor ST was Obtained by the Following Steps (1) 0.5 g of commercially-available hydroxyacetic acid (with water content of approximately 1%) was weighed and dissolved in in 2.2 mL of trifluoroacetic acid; 5 mg of aflatoxin biosynthetic precursor ST was weighed and dissolved in 2.2 mL of acetonitrile; the solution of aflatoxin biosynthetic precursor ST in acetonitrile was drawn with a syringe, and pipetted gently into the mixture of hydroxyacetic acid/trifluoroacetic acid and reacted at room temperature for 5 h with magnetic stirring; the solvent was evaporated rotationally, yielding a light yellowish green oily substance which was the aflatoxin biosynthetic precursor ST hapten.

(2) 5.3 mg of aflatoxin biosynthetic precursor ST hapten and 17 mg of N-hydroxylsuccinimide were weighed and placed into a reaction flask, and reacted at room temperature for 1.5 h with magnetic stirring; 26 mg of carbodiimide was weighed and dissolved in 0.7 mL of 1,4-dioxohextane; the solution of carbodiimide in 1,4-dioxohextane was added slowly dropwise into the reaction flask and reacted at room temperature for 4.5 h with magnetic stirring until a white precipitate was generated in the reaction flask; after completion of the reaction, the reactants were kept at room temperature overnight, in the next day, the reactants were subjected to centrifugation at 8000 r/min for 5 min, and the supernatant was obtained; 18 mg of ovalbumin (OVA) was weighed and dissolved in 6.5 mL of PBS buffer (0.2 mol/L, pH8.0), the above-obtained supernatant was added dropwise into the solution of OVA in PBS; after finishing the addition of the supernatant, the reaction was run for 4.5 h, yielding an complete antigen of aflatoxin biosynthetic precursor ST in aqueous phase.

(3) The complete antigen of aflatoxin biosynthetic precursor ST in aqueous phase obtained from the above-mentioned step (2) was sealed into a dialysis bag and dialyzed for a total of 3 days against 0.015 mol/L, pH8.0 phosphate buffer, where the dialysis solution was replaced once every 8 h; after completion of the last dialysis, the solution in the dialysis bag was divided into fractions, placed in centrifuge tubes, and lyophilized to yield the artificial antigen of aflatoxin biosynthetic precursor ST.

EXAMPLE 3

An Artificial Antigen of Aflatoxin Biosynthetic Precursor ST was Obtained by the Following Steps (1) 1 g of commercially-available hydroxyacetic acid (with water content of approximately 1%) was weighed and dissolved in 4 mL of trifluoroacetic acid; 10 mg of aflatoxin biosynthetic precursor ST was weighed and dissolved in 4 mL of acetonitrile; the solution of aflatoxin biosynthetic precursor ST in acetonitrile was drawn with a syringe, and pipetted gently into the mixture of hydroxyacetic acid/trifluoroacetic acid and reacted at room temperature for 6 h with magnetic stirring; the solvent was evaporated rotationally, yielding a light yellowish green oily substance which was the aflatoxin biosynthetic precursor ST hapten.

(2) 10 mg of aflatoxin biosynthetic precursor ST hapten and 30 mg of N-hydroxylsuccinimide were weighed and placed into a reaction flask, and reacted at room temperature for 2 h with magnetic stirring; 45 mg of carbodiimide was weighed and dissolved in 1.2 mL of 1,4-dioxohextane; the solution of carbodiimide in 1,4-dioxohextane was added slowly dropwise into the reaction flask and reacted at room temperature for 5 h with magnetic stirring until a white precipitate was generated in the reaction flask; after completion of the reaction, the reactants were kept at room temperature overnight, in the next day, the reactants were subjected to centrifugation at 8000 r/min for 5 min, and the supernatant was obtained; 30 mg of hemocyanin (KLH) was weighed and dissolved in 8 mL of PBS buffer (0.2 mol/L, pH8.0), the above-mentioned supernatant was added dropwise into the solution of KLH in PBS; after finishing the addition of the supernatant, the reaction was run for 5 h, yielding an complete antigen of aflatoxin biosynthetic precursor ST in aqueous phase.

(3) The complete antigen of aflatoxin biosynthetic precursor ST in aqueous phase obtained from the above-mentioned step (2) was sealed into a dialysis bag and dialyzed for a total of 3 days against 0.02 mol/L, pH8.0 phosphate buffer, where the dialysis solution was replaced once every 4 h; after completion of the last dialysis, the solution in the dialysis bag was divided into fractions, placed into centrifuge tubes, and lyophilized to yield the artificial antigen of aflatoxin biosynthetic precursor ST.

Identification of the artificial antigen according to certain embodiments of the present invention is as follows.

1. The artificial antigen of aflatoxin biosynthetic precursor ST was identified by the ultraviolet-visible spectrum continuous scanning profile. As shown in FIG. 1, the artificial antigen of aflatoxin biosynthetic precursor ST was coupled successfully to the carrier protein, bovine serum albumin. From the absorbance value and the extinction coefficient at the characteristic ultraviolet absorption wavelength of 413 nm for the conjugate, the coupling ratio between the aflatoxin biosynthetic precursor ST and the bovine serum albumin is calculated to be 3.4:1.

2. Immunization in animal had confirmed that anti-aflatoxin biosynthetic precursor ST antibodies were produced.

(1) Immunological experiment in mice: the above-mentioned synthesized aflatoxin biosynthetic precursor ST-bovine serum albumin was formulated with 0.85% of physiological saline into a solution of 0.67 mg/mL. The first immunization was performed by mixing 0.45 mL Freund's complete adjuvant with an equal volume of the formulated aflatoxin biosynthetic precursor ST-bovine serum albumin mentioned above and fully emulsifying the mixture, followed by subcutaneous injection of 0.3 mL of the preparation (equivalent to 100 μg protein) into each of the 6-8 weeks-old Balb/c mice. Immunization was boosted 1 time every 3 weeks and in the booster immunization, the adjuvant would be changed to Freund's incomplete adjuvant with the remaining of the procedure being the same as those in the first immunization method. Blood was drawn from the tail of the mouse 7-10 days after each booster immunization and the antisera were prepared.

(2) Determination of the antibody titer by non-competitive ELISA assay: the coated antigen, aflatoxin biosynthetic precursor ST-bovine serum albumin, was diluted with a pH9.6 carbonate salt buffer to 0.5 μg/mL. 100 μl of the diluted solution was added into each of the wells of the ELISA plate. The plate was incubated at 4° C. overnight, and then the coating solution was poured off. Each well was washed three times with a typical phosphate-Tween washing liquid and dripped to dry. 200 μl of 1.5% skimmed milk solution was added into each well and the plate was blocked at 37° C. for 2 h. The blocking solution was poured off, and each well was washed three times and dripped to dry. The antiserum was subjected to double dilution starting from 500 folds, and each well was added with 100 μl. The control wells were set up in parallel with negative serum as the negative control and 0.15 mol/L, pH7.4 phosphate buffer as the blank control. The plate was incubated and moisturized at 37° C. for 2 h, washed three times, and dripped to dry. 100 μl of the enzymatically labelled goat-anti-mouse secondary antibody IgG:HRP diluted at 1:5000 with 0.15 mol/L, pH7.4 phosphate buffer was added into each well, and incubated and moisturized at 37° C. for 2 h. Each well was washed six times and dripped to dry. 100 μl of the reactive substrate solution was added into each well and reacted at 37° C. in the dark for 10-15 min. Then, 50 μl of the 2 mol/L sulphuric acid solution was added into each well to stop the reaction. After 5 min, zero is set using the blank control well, and the absorbance value was measured at 450 nm. The antiserum titer was the dilution factor of the antiserum corresponding to the measured absorbance value of the antiserum two times that of the negative serum.
The results were listed in Table 1.

TABLE 1

The antiserum titer against aflatoxin biosynthetic precursor ST

| | Dilution fold | | | | | | | | Negative control |
|---|---|---|---|---|---|---|---|---|---|
| | 1250 | 2500 | 5000 | 10000 | 20000 | 40000 | 80000 | 160000 | |
| Absorbance | 1.16 | 1.14 | 1.07 | 0.85 | 0.62 | 0.43 | 0.39 | 0.14 | 0.09 |

From the data in Table 1, it can be proved that the artificial antigen of aflatoxin biosynthetic precursor ST prepared according to the method of the invention can produce an antiserum with a titer of greater than 80000 after immunization.

(3) ELISA competitive inhibition assay: the operation steps in the ELISA assay were the same as above, except that the antisera subjected to double dilution were replaced with the antiserum solutions containing different concentrations of the standard of the aflatoxin biosynthetic precursor ST. It would confirm that the antibodies in the antisera was capable of binding to the aflatoxin biosynthetic precursor ST if the absorbance value was decreased with increase in the concentrations of the standard of the aflatoxin biosynthetic precursor ST. Results obtained from the competitive ELISA assay were shown in the following Table 2:

TABLE 2

ELISA competitive inhibition assay results against aflatoxin biosynthetic precursor ST

| | Inhibition concentrations for aflatoxin biosynthetic precursor ST (ng/mL) | | | | | | | | | |
|---|---|---|---|---|---|---|---|---|---|---|
| | 0 | 0.01 | 0.04 | 0.14 | 0.41 | 1.23 | 3.70 | 11.1 | 33.3 | 100 |
| Absorbance | 0.90 | 0.82 | 0.75 | 0.66 | 0.49 | 0.34 | 0.11 | 0.03 | 0.01 | 0 |

Results of competitive ELISA inhibition assay in Table 2 indicates that the antibody against aflatoxin biosynthetic precursor ST had been produced in the mice, thereby demonstrating that the artificial antigen of aflatoxin biosynthetic precursor ST prepared according to the method in the present invention is successful. Further, it can be seen from Table 2 that $IC_{50}$ value of the antibody for the aflatoxin biosynthetic precursor ST is 0.41 ng/mL. It demonstrates that antibodies with high-sensitivity can be produced after immunization of the mice with the artificial antigen of aflatoxin biosynthetic precursor ST synthesized according to the method in the present invention.

(4) Antibody specificity assay: the operation steps of ELISA were the same as above, except that the antisera subjected to double dilution were replaced with the antiserum solutions containing different concentrations of the standards of aflatoxins B1, B2, G1, and G2. It would confirm that the antibodies in the antisera did not bind to aflatoxins B1, B2, G1, and G2 if there were no regular changes in the absorbance values with the increase in the concentrations of the standards of aflatoxins B1, B2, G1, and G2. Results obtained from the competitive ELISA assay were shown in the following Table 3.

TABLE 3

ELISA competitive inhibition assay against aflatoxins B1, B2, G1, and G2

| | Inhibition concentrations for aflatoxin B1 (ng/mL) | | | | | | | | | |
|---|---|---|---|---|---|---|---|---|---|---|
| | 0 | 0.01 | 0.04 | 0.14 | 0.41 | 1.23 | 3.70 | 11.1 | 33.3 | 100 |
| Absorbance | 0.99 | 1.01 | 0.95 | 0.93 | 1.05 | 0.97 | 0.92 | 0.96 | 0.99 | 0.94 |
| | Inhibition concentrations for aflatoxin B2 (ng/mL) | | | | | | | | | |
| | 0 | 0.01 | 0.04 | 0.14 | 0.41 | 1.23 | 3.70 | 11.1 | 33.3 | 100 |
| Absorbance | 1.04 | 1.06 | 0.99 | 1.07 | 1.01 | 1.02 | 1.04 | 1.01 | 1.02 | 1.08 |
| | Inhibition concentrations for aflatoxin G1 (ng/mL) | | | | | | | | | |
| | 0 | 0.01 | 0.04 | 0.14 | 0.41 | 1.23 | 3.70 | 11.1 | 33.3 | 100 |
| Absorbance | 1.02 | 1.07 | 1.05 | 1.01 | 0.98 | 1.04 | 1.09 | 1.11 | 1.05 | 1.07 |
| | Inhibition concentrations for aflatoxin G2 (ng/mL) | | | | | | | | | |
| | 0 | 0.01 | 0.04 | 0.14 | 0.41 | 1.23 | 3.70 | 11.1 | 33.3 | 100 |
| Absorbance | 1.08 | 1.04 | 1.05 | 1.04 | 1.01 | 1.09 | 1.02 | 1.10 | 1.01 | 1.03 |

Results of the experiment on the specificity of the antibody in Table 3 indicated that the antibody produced in the mice did not bind to aflatoxins B1, B2, G1, and G2, which demonstrated that antibodies with high specificity can be produced after immunization of the mice with the artificial antigen of aflatoxin biosynthetic precursor ST synthesized according to the method in the present invention.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments are chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. An artificial antigen of aflatoxin biosynthetic precursor Sterigmatocystin (ST), having a structure of formula (I), formula (I)

wherein Me is methyl group, and CP is a carrier protein.

2. A method for preparing the artificial antigen of aflatoxin biosynthetic precursor ST of claim 1, comprising:
   weighing 0.1-1 gram (g) of hydroxyacetic acid and dissolving the weighed hydroxyacetic acid in 0.4-4 milliliter (mL) of trifluoroacetic acid to obtain a mixture of hydroxyacetic acid/trifluoroacetic acid;
   weighing 1-10 milligram (mg) of aflatoxin biosynthetic precursor ST and dissolving the weighed aflatoxin biosynthetic precursor ST in 0.4-4 mL of acetonitrile to obtain a solution of aflatoxin biosynthetic precursor ST in acetonitrile;
   drawing the solution of aflatoxin biosynthetic precursor ST in acetonitrile with a syringe and pipetting gently into the mixture of hydroxyacetic acid/trifluoroacetic acid, and allowing a reaction to run at room temperature for 4-6 hours under stirring;
   after completion of the reaction, evaporating rotationally the solvent to obtain a light yellowish green oily substance which is the aflatoxin biosynthetic precursor ST hapten;
   weighing 1-10 mg of the aflatoxin biosynthetic precursor ST hapten and 4-30 mg of N-hydroxylsuccinimide, placing into a reaction flask, and reacting for 1-2 hours;
   weighing 7-45 mg of carbodiimide and dissolving in 0.2-1.2 mL of 1,4-dioxohextane to obtain a solution of carbodiimide in 1,4-dioxohextane, adding the solution of carbodiimide in 1,4-dioxohextane dropwise into the reaction flask, reacting at room temperature for 4-5 hours until a white precipitate is generated in the reaction flask, after completion of the reaction, keeping reactants in the reaction flask at room temperature overnight, and on the next day, centrifuging the reactants in the reaction flask to obtain a supernatant; and
   adding the supernatant dropwise into a phosphate buffered saline (PBS) solution having 4-30 mg of the carrier protein dissolved therein, after the supernatant is added completely, allowing the reaction to run for 4-5 hours to obtain a complete antigen of aflatoxin biosynthetic precursor ST in aqueous phase.

3. The method for preparing the artificial antigen of aflatoxin biosynthetic precursor ST of claim 2, wherein the PBS solution is 5-8 mL of a 0.2 mol/L, pH8.0 phosphate buffer.

* * * * *